United States Patent

Dai et al.

[11] Patent Number: 6,160,026
[45] Date of Patent: Dec. 12, 2000

[54] PROCESS FOR OPTIMIZING HYDROCARBON SYNTHESIS

[75] Inventors: Pei-Sing Dai, deceased, late of Port Authur, by Yih-Yin Doris Dai, executor; Jeffrey B. Harrison, The Woodlands; Govanon Nongbri, Houston; Lalit Shah; Kamlesh B. Vakil, both of Sugarland, all of Tex.

[73] Assignee: Texaco Inc., White Plains, N.Y.

[21] Appl. No.: 09/158,161

[22] Filed: Sep. 22, 1998

Related U.S. Application Data

[60] Provisional application No. 60/059,913, Sep. 24, 1997.

[51] Int. Cl.[7] .................................................. C07C 27/00
[52] U.S. Cl. ........................ 518/712; 518/700; 518/705; 518/715
[58] Field of Search ...................... 518/700, 712, 518/715, 705

[56] References Cited

U.S. PATENT DOCUMENTS

| | | | |
|---|---|---|---|
| 4,312,741 | 1/1982 | Yves | 208/11 |
| 4,521,295 | 6/1985 | Chervenak et al. | 208/59 |
| 4,548,702 | 10/1985 | York et al. | 208/11 R |
| 4,585,798 | 4/1986 | Beuther et al. | 518/715 |
| 4,857,559 | 8/1989 | Eri et al. | 518/700 |
| 4,874,583 | 10/1989 | Colvert | 422/143 |
| 4,880,763 | 11/1989 | Eri et al. | 502/302 |
| 4,946,477 | 8/1990 | Perka et al. | 48/197 R |
| 4,980,145 | 12/1990 | Hsiung et al. | 423/437 |
| 5,108,580 | 4/1992 | Nongbri et al. | 208/61 |
| 5,218,003 | 6/1993 | Lewnard et al. | 518/700 |
| 5,252,613 | 10/1993 | Chang et al. | 518/700 |
| 5,302,622 | 4/1994 | Chaumette et al. | 518/713 |
| 5,776,988 | 7/1998 | Chaumette et al. | 518/715 |

FOREIGN PATENT DOCUMENTS

| | | |
|---|---|---|
| 773274A1 | 5/1997 | United Kingdom . |
| WO 98/06487 | 2/1998 | United Kingdom ......... 8/22 |

*Primary Examiner*—Johann Richter
*Assistant Examiner*—J. Parsa
*Attorney, Agent, or Firm*—Harold J. Delhommer; Arnold, White & Durkee

[57] ABSTRACT

The invention is a process for producing hydrocarbons from hydrogen and carbon monoxide by reacting hydrogen and carbon monoxide in the presence of a particulate solid catalyst and a substantially inert liquid medium. This reaction takes place in a reactor vessel adapted for the reaction of gases in the presence of a substantially inert liquid medium and a bed of solid particulate catalyst. The hydrogen gas and carbon monoxide gas are introduced at a plurality of locations within the reactor vessel. Bubbles of gas flow upward through the bed of solid catalyst particles and substantially inert liquid medium at sufficient velocity to expand the bed to a volume greater than its static volume. This velocity creates a turbulent reaction zone wherein liquid, gas, and solid catalyst are present and are in a state of motion.

27 Claims, 3 Drawing Sheets

PROCESS FOR OPTIMIZING HYDROCARBON SYNTHESIS

CROSS REFERENCE TO PATENTS

This application claims priority from U.S. provisional patent application serial No. 60/059,913 filed on Sep. 24, 1997, entitled PROCESS FOR OPTIMIZING HYDROCARBON SYNTHESIS.

FIELD OF THE INVENTION

This invention relates to the production of hydrocarbons from hydrogen gas and carbon monoxide gas. Specifically, the invention relates to such hydrocarbon production in an ebullated bed.

BACKGROUND OF THE INVENTION

The reaction to convert carbon monoxide and hydrogen mixtures (defined herein as synthesis gas) to hydrocarbons over metallic catalysts has been known since the turn of the century. This reaction is commonly referred to as the Fischer-Tropsch or F-T synthesis. The synthesis gas used as feed to the process can be obtained from any source known to those skilled in the art, such as, for example, steam reforming of natural gas or partial oxidation of coal.

An important criterion for commercial F-T synthesis is having the ability to control the temperature of the reactants. The F-T reaction is highly exothermic. The efficient and rapid removal of heat is a major consideration in the generation of high molecular weight hydrocarbons. Unfortunately, high temperatures, i.e. above 325° C., often lead to methane generation, carbon deposition on the catalyst, and catalyst particle fragmentation. Methane generation is usually not desired because the yield of higher hydrocarbons is reduced. Carbon deposition and catalyst particle fragmentation is undesirable because the catalyst life is shortened.

The prior art addressed the heat generation problem of the highly exothermic F-T reaction by using long tubular reactors that have a greater surface area to volume ratio than more conventional cylindrical reactors, thereby utilizing the additional surface area for cooling. Another method used by prior art is to run the reaction at low conversion rates per pass through the reactor, thereby using the unreacted gas to remove heat.

The temperature gain may also be controlled by utilizing a slurry bed reactor. The major drawbacks to the commercialization of the slurry bed reactor processes in the prior art are the separation of wax products and fine catalyst particles, and the mechanical failure due to high erosion of pump equipment used to re-circulate the slurry to the reactor zone.

Another problem with F-T commercialization is efficient conversion of reactants. The F-T synthesis generally utilizes hydrogen and carbon monoxide at a molar ratio of just over 2.0:1. Stoichiometrically, one hydrogen molecule combines with the carbon to form hydrocarbon and a second hydrogen molecule combines with the oxygen to form water vapor. The gas in the reactor can become depleted in one reactant, which will slow the reaction rate to levels below commercial viability. The reduction in the reaction rate is exacerbated when the reactant that is deficient in hydrogen. There are many different catalysts available for an F-T synthesis, and the effect of a deficiency in a reactant on the reaction rates varies among these catalysts. However, the effect of a deficiency in hydrogen gas is always more pronounced than is the effect of a deficiency in carbon monoxide. For instance, the F-T reaction rate with a cobalt based catalyst increases with both the partial pressure of hydrogen and of carbon monoxide; however, changes in the partial pressure of hydrogen have almost twice the effect as changes in the partial pressure of carbon monoxide. The reaction rate therefore drops off twice as fast when the synthesis gas is deficient in hydrogen as compared to the reaction rate decline caused by a deficiency in carbon monoxide.

This is usually not problematic if the ratio of hydrogen to carbon monoxide in the synthesis gas is about 2.1:1 and there is little methane synthesis. However, to obtain a greater fraction of waxy hydrocarbon product, a hydrogen to carbon monoxide ratio below a 2.1:1 ratio may be required. Therefore, as an F-T synthesis of waxy hydrocarbons reaction proceeds and the synthesis gas is converted to hydrocarbons, the synthesis gas can become progressively depleted in hydrogen. This results in a substantial portion of the hydrogen gas, carbon monoxide gas, or both, leaving the reactor without being converted.

Another related problem is that as the reactant gases become converted into hydrocarbons and water, diluent gases in the feed gas stream, e.g. water vapor, light hydrocarbons, and contaminants, may dilute the hydrogen gas and the carbon monoxide gas to the point that the reaction rate is significantly reduced. This further exacerbates the reduction in rate that is experienced when a reactant becomes deficient.

Finally, in typical reactors where a reactant is gas, the gas distribution in the reaction zone and back mixing are primary factors that determine reactor performance. Poor gas distribution will result in slug flow in slurry reactors or channeling in tubular reactors that results in reactant gases not uniformly exposed to catalyst. Gas maldistribution may result in a hot spot in the reactor which favors the undesired methanation reaction and may damage the catalyst. Back mixing will reduce the kinetic performance. Such maldistribution and back mixing often occur in conventional F-T processes.

It would be desirable if an F-T process could be developed which provides sufficient temperature control so as to avoid methanation, catalyst deactivation through carbon deposition, and catalyst fragmentation. It would further be desirable if such a process offered a manner of maintaining a hydrogen to carbon monoxide ratio other than the stoichiometric ratio of 2.1:1. It would still further be desirable if such a process offered a means of distributing the reactant gases in the catalyst bed in such a manner to reduce channeling or back-mixing.

SUMMARY OF THE INVENTION

The invention is a process for producing hydrocarbons from hydrogen and carbon monoxide by reacting hydrogen and carbon monoxide in the presence of a particulate solid catalyst. This reaction takes place in a reactor vessel adapted for the reaction of gases in the presence of a substantially inert liquid medium and a bed of solid particulate catalyst, i.e. in an ebullated bed reactor. The hydrogen gas, the carbon monoxide gas, or both, are introduced at a plurality of locations within the reactor vessel. Liquid medium is introduced at least one location in the reactor vessel and is generally well mixed with gas before entering the reaction zone. Bubbles of gas and substantially inert liquid medium flow through the bed of solid catalyst particles at sufficient velocity to expand the reaction zone to a volume greater than its static volume. This velocity creates a turbulent reaction zone wherein liquid, gas, and solid catalyst are present and are in a constant state of motion.

The process employed in the present invention is often described as an ebullated bed process. The ebullated bed process comprises the passing of substantially concurrently flowing streams of liquids and gas through a vertical cylindrical vessel containing catalyst particles. The catalyst is in motion in the fluid comprised of liquid and gas bubbles. The catalyst bed motion is controlled by the gas flow and by the liquid flow, so that at steady state the bulk of the catalyst is controlled to a definable level in the reactor.

The ebullated bed process of the present invention provides multiple options for temperature control and catalyst level control while maintaining very high throughput and conversion. Heat is removed in a variety of ways, including control of the feed gas preheat to a desired temperature, internal heat exchangers, removal of a stream of liquid medium and product for cooling and either returning cooled liquid medium or adding liquid medium from another source to the reactor. In addition, the sensible and latent heat capacity of the liquid medium moderates temperature changes.

The reactor fluid provides a convenient means of removing product from the reactor. In addition, the motion of catalyst in the reactor provides a convenient means for removing catalyst while the reactor is on stream. The rate of catalyst addition and withdrawal is used to control catalyst activity.

The introduction of gas at a plurality of locations within the reactor provides a means to supplement the gas within the reactor with hydrogen gas, carbon monoxide gas, or other gases, or of mixtures thereof, at predetermined points in the reactor. This supplemental gas is used to maintain the optimum hydrogen to carbon monoxide ratio so that the selectivity of the catalyst is toward making the desired product, which in a preferred embodiment of this invention is a waxy paraffin. This supplemental gas is used to maintain the partial pressure of both carbon monoxide and of hydrogen in order to facilitate a high but controlled rate of reaction. Furthermore, this supplemental gas injection will improve gas distribution throughout the bed and help prevent undesirable back-mixing.

Another commercial application of the F-T synthesis process produces principally fuels as products.

Figure 3:
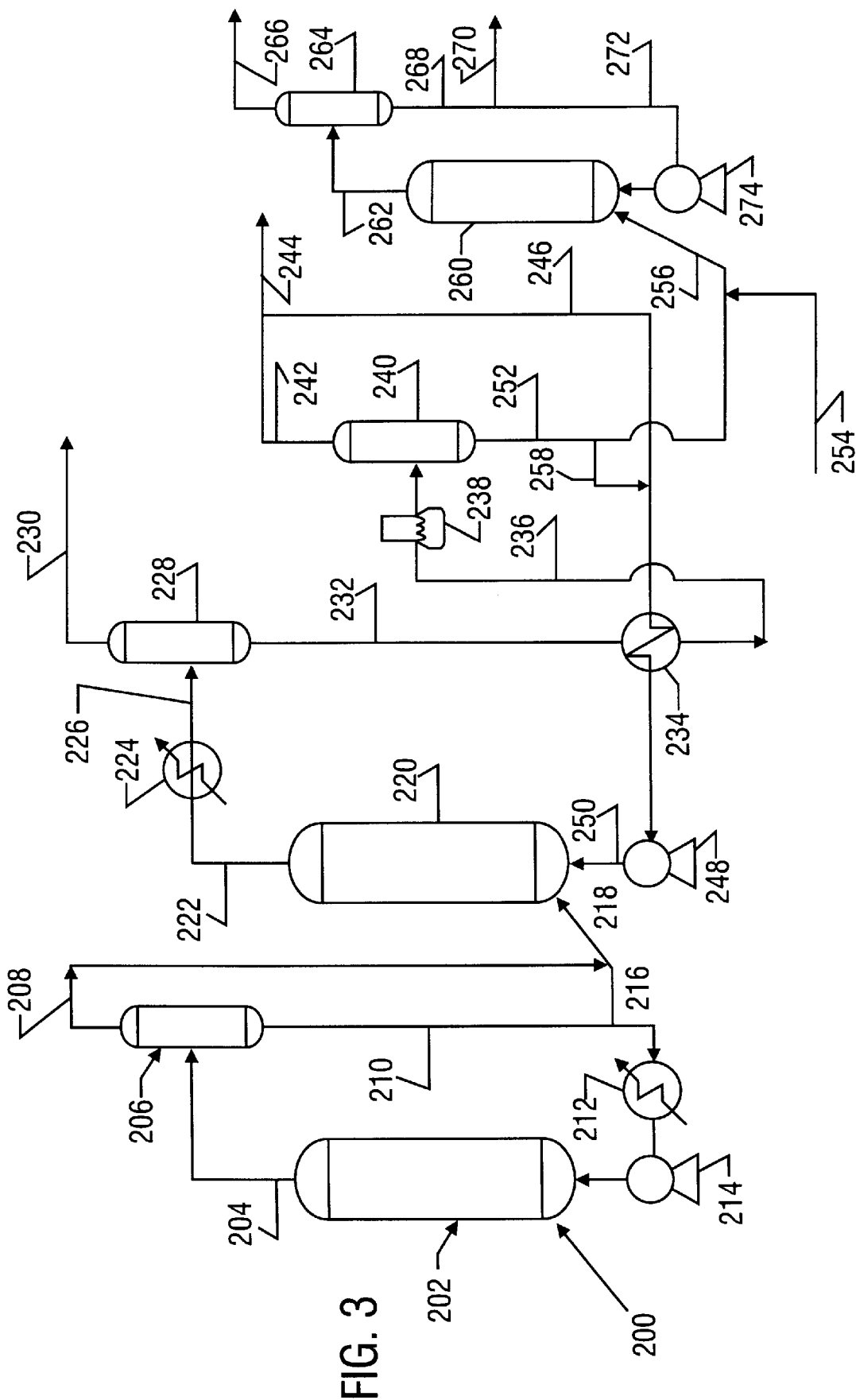

FIG. 3 is a schematic of such a process wherein three reactors in series are used to process the feed synthesis gas. In this scheme, the F-T synthesis occurs in the first two reactors. The function of the third reactor is not an F-T synthesis but rather to crack high molecular weight hydrocarbons into lower molecular weight hydrocarbons.

DETAILED DESCRIPTION OF THE INVENTION

As used herein, the term "reactant gas" refers to either carbon monoxide gas or hydrogen gas, or to a mixture of both. The mixture which comprises these gases is often referred to as "synthesis gas" or "syngas." A synthesis gas may also contain inert compounds and contaminants. Examples of inert compounds include carbon dioxide, nitrogen gas, and methane. Carbon dioxide and methane are usually not desired feed components for use with the process of this invention, but in minor amounts they usually do not adversely affect the process, other than acting as a diluent. Examples of contaminants include molecular oxygen, metal carbonyl compounds, water vapor and sulfur-containing compounds. The presence of water vapor, a product of the F-T reaction, in the feed gas will slightly reduce the equilibrium conversion of the reactant gases, but this minor quantity has little practical effect in a commercial reactor wherein large quantities of water are generated. Sulfur-containing compounds and metal carbonyl compounds, on the other hand, can poison a catalyst and should be kept to a minimum.

As used herein, the term "hydrocarbons" is used generically and refers to compounds containing hydrogen and carbon. This includes straight chain hydrocarbons, cyclical hydrocarbons, branched hydrocarbons, saturated or paraffinic hydrocarbons, unsaturated hydrocarbons, olefins, oxygenates and other compounds which contain predominantly hydrogen and carbon. Paraffinic hydrocarbons are the most common products, while aromatic hydrocarbons are generally not included.

As used herein, the term "substantially inert liquid medium" and "liquid medium" refer to a hydrocarbon or a mixture of hydrocarbons that serves as the continuous phase in the reaction zone, as a means to suspend the catalyst particles, as a receptor for the heat of reaction, and as a carrier for the product hydrocarbons. The liquid medium may react with the catalyst and the reactant gases under reactor conditions. This is usually only a minor reaction, and generally most reactant gas forms hydrocarbons without using a molecule from the liquid medium as a base. Both the reactant gases and the product have some solubility in the substantially inert liquid medium. In fact, the product of the synthesis reaction is a mixture of hydrocarbons which may be indistinguishable from and used as a liquid medium, or, alternatively, certain fractions of the product of the synthesis reaction may be used as the liquid medium.

As used herein, the terms "reaction zone" and "reaction volume" refer to a volume in the reactor that comprise synthesis gas bubbles, solid particulate catalyst, and substantially inert liquid. Each of these components must have a fraction that is in turbulent motion.

The invention is a process for producing hydrocarbons from hydrogen and carbon monoxide by reacting hydrogen and carbon monoxide in the presence of a particulate solid catalyst in a manner which effectively controls the exothermic heat of reaction. This reaction takes place in a reactor vessel adapted for the reaction of gases in the presence of a substantially inert liquid medium and a bed of solid particulate catalyst. The hydrogen gas and carbon monoxide gas, or more often a synthesis gas comprising both gases, are introduced at a plurality of locations within the reactor vessel. Substantially inert liquid is also introduced at least one location in the reactor and liquid flow is substantially concurrent with gas flow. Bubbles of gas and substantially inert liquid medium flow upward through the zone containing solid catalyst particles at sufficient velocity to expand the zone to a volume greater than its static volume. The velocity of the fluids creates a turbulent reaction zone wherein liquid, gas, and solid catalyst are present and are in a state of motion. The velocity of gas and liquid are preferably controlled so that the reaction can proceed efficiently but the catalyst does not exit the reaction zone with the gas and the liquid stream or streams.

The reactor is an ebullated bed reactor. The ebullated bed comprises a liquid medium, catalyst particles, and gas bubbles. The ebullated bed has sufficient gas space velocity from the upward flow of gas bubbles and liquid medium to cause the bed to expand to a volume greater than its static volume, thereby creating a turbulent reaction zone wherein at least some of the solid catalyst is in a state of motion. Gaseous space velocity, i.e. the gas throughput divided by the total volume of the reactor that contains gas, should be between 200 and 20,000 $m^3$ per $m^3$ catalyst per hour and preferably between 500 and 10,000 $m^3$ per $m^3$ catalyst per hour. This gas space velocity allows high conversion of synthesis gas to liquids. This gas space velocity is higher than is normally observed in ebullated beds. This high throughput and conversion is possible because of the heat removal efficiency of the preferred embodiments.

Ebullated beds also depend on fluid circulation to expand the bed. Liquid medium is introduced, flows substantially concurrently with the gas, and this fluid velocity increases the ebullated bed height and the motion of the three phases. In the preferred embodiment the combined flow of gas and liquid are sufficient to expand the bed to the point wherein a substantial portion, i.e. greater than 90%, of the solid catalyst is in a state of motion, but the ebullated bed volume is controlled to a predetermined amount of expansion.

The reactant gases may be introduced anywhere in the reactor so long as they contact the catalyst and liquid medium. Since bubbles move up, it is usually advantageous to locate a means of introducing reactant gases near the bottom of the reactor to utilize the maximum reactor volume. The introduction of gas near the bottom of the reactor can be by any means known to the art. Typically, a means is selected such that bubbles are formed with an average diameter of less than 5 millimeters, preferably less than 3 millimeters, and most preferably less than 1 millimeter. In addition to the means of distribution, bubble size is also a factor of the viscosity, surface tension, and molecular weight of the liquid medium and of the relative fraction of catalyst particles to the liquid medium. Those skilled in the art can readily influence bubble size by varying liquid properties, gas rates, solid catalyst concentrations, and gas distribution methods.

A particularly preferred means for introducing gas is a transverse distributor plate which introduces both liquid medium and a gas comprising the reactant gases uniformly across the bottom of the expanded bed to maintain a stable yet turbulent flow within the bed. The transverse distributor plate also serves as a partition to separate the substantially inert liquid and gas feed streams from the expanded catalyst bed and provides physical support for the ebullated catalyst bed within the reactor. This preferred means is described in U.S. Pat. No. 4,874,583, which is incorporated herein by reference. Below this distributor plate those skilled in the art may have spargers or other mechanical devices to dissipate the kinetic energy of the feed gas and, if necessary, the liquid. This distributor plate injects fluids and gas into a reaction zone comprising the fluid, the catalyst particles, and bubbles of gas.

The reaction zone extends, without interruption, from about the lowest point in the reactor where gas is injected into the bed that contains liquid medium and solid particulate catalyst to about the substantially catalyst free separation zone near the top of the reactor. Generally in large reactors the reactor volume is segregated by plates. Each plate can function to redistribute fluids and to support the catalyst. However, substantial reactor volume is lost, because each plate generally must be preceded by a separation zone. In this invention there are no plates or other mechanical devices which may isolate sections of the reactor but only at a cost of a loss of substantial reactor volume. The entire volume within the uninterrupted reaction zone is available for catalyst particles in a liquid medium to contact gas bubbles. The weight of the catalyst load is lessened both by buoyancy in the liquid medium and by the lift created by the upward flowing gas and liquid. Fluids are added from below and withdrawn from the top of this reaction zone. The additional locations where reactant gases are introduced are positioned such that gas is introduced into the existing reaction zone. The reaction zone does not include volume occupied by heat exchangers.

The fraction of the reaction zone occupied by solid catalyst ranges from about 10 to about 60 percent of the total reaction volume. A preferred embodiment has the fraction of the reaction zone occupied by solid catalyst ranging from about 10 to about 50 percent of the total reaction volume. A more preferred embodiment has the fraction of the reaction zone occupied by solid catalyst ranging from about 10 to about 40 percent of the total reaction volume. The substantially inert liquid medium and gas bubbles will occupy the remaining reaction zone volume. The preferred fraction of the reaction zone occupied by the substantially inert liquid medium will be from about 30 to about 80 percent of the total reaction zone volume. The most preferred fraction of the reaction zone occupied by the substantially inert liquid medium will be from about 50 to about 70 percent of the total reaction zone volume. The fraction of the reaction zone normally occupied by gases will be the balance not occupied by solid catalyst or the liquid medium. The preferred fraction of the reaction zone occupied by gas bubbles will be from about 5 to about 50 percent of the total reaction zone volume. The more preferred fraction of the reaction zone occupied by gas will be from about 20 to about 45 percent of the total reaction zone volume. The most preferred fraction of the reaction zone occupied by gas will be from about 20 to about 40 percent of the total reaction zone volume.

Near the top of the ebullated bed reactor is a substantially catalyst free zone that functions as a separation zone for catalyst from the gas and liquid phases in the ebullated bed. This separation zone is often from about one tenth to about one third of the reactor volume. The liquid medium and gases pass overhead to a hot separator where they can be treated outside of the reactor. Depending on the amount of reactant gases present, one skilled in the art may recycle a portion of the separated gas through the reactor, or use this gas in a subsequent reactor, or use this gas as fuel. Examples of treatment can include removing product, removing some fraction of the liquid medium by any means known to the art, cooling the medium, or filtering fines from the medium. A preferred embodiment of this invention introduces this treated liquid medium back into the reactor.

The reactor contains means for introducing gas comprising one or both reactant gases at a plurality of locations within the single reaction zone. One of these locations is that previously discussed near the bottom of the reaction zone, since the bubbles tend to rise through the bed. The other means may be located throughout the reaction zone. In a preferred embodiment synthesis gas injected at the bottom-most gas injection means, has a molar ratio of hydrogen to carbon monoxide that is between 0.5:1 to about 6.0:1, preferably between 1.0:1 to 3.0:1; and more preferably between 1.6:1 to 2.2:1. This most preferred ratio generally gives a good reaction rate with a cobalt based catalyst and gives higher selectivity to the desired heavier hydrocarbon product.

The stoichiometric ratio of hydrogen to carbon monoxide usage within the process can range from about 2:1 for waxy hydrocarbon generation to about 3:1 for methane generation. It is clear that as the reactants are converted, and some methane is inevitably generated, the gas will soon become deficient in a reactant gas, i.e. hydrogen, and the ratio of hydrogen to carbon monoxide moves outside the desired range in the absence of supplemental gas. There is at least one additional means to introduce gas into the reaction zone at a location above the lowest point where gas is injected. Each of said additional means of introducing gas is located within the reactor vessel at a predetermined distance from the bottom of the vessel. The exact locations of the additional means for introducing gas into the reaction zone will usually be chosen to maximize reactor efficiency and reaction selectivity.

In a preferred embodiment, the additional means to introduce additional reactant gases within the single turbulent reaction zone is an apparatus comprising a sparger attached to a tube. Said spargers are designed and positioned to minimize back mixing of the reactant gases. Each of these means for introducing synthesis gas dispenses gas at a plurality of points, and all of said points are located at approximately the same distance from the bottom of the reactor vessel, are approximately equidistant from a vertical axis defined by the centers of the horizontal cross sections of the reactor vessel, and are arranged with approximate radial symmetry about said vertical axis. Proper placement of spargers will reduce back-mixing, encourage even distribution of gas bubbles, and control bubble size growth in the reaction zone. The reduction of back mixing in the ebullated bed reactor will allow the unit to attain efficient conversion of the hydrogen and carbon monoxide to product.

The number of locations where said additional gas will be introduced will vary from about 1 to about 15. A preferred embodiment would contain from 2 to 9 locations wherein additional gas is introduced into the reaction zone, while a more preferred embodiment would contain from 3 to 8 locations, and the most preferred embodiment would contain from 6 to 7 locations. In the preferred embodiment the positioning of these locations and the amount of hydrogen gas or carbon monoxide gas, or both, introduced is sufficient to preserve relatively constant hydrogen to carbon monoxide ratio from about 0.5:1 to about 6.0:1, more preferably from about 1.0:1 to about 3.0:1, and most preferably from about 1.6:1 to about 2.2:1, through the reaction zone.

As conversion of the synthesis gas to hydrocarbons proceeds, the reaction rate will drop off as the hydrogen gas content of the synthesis gas in the ebullated bed becomes depleted. The carbon monoxide content of the synthesis gas in the ebullated bed is also becoming depleted, though at a lower rate than is the hydrogen. As conversion proceeds, the initial diluents such as carbon dioxide, nitrogen and methane become more predominate. In addition, some of the products of the F-T synthesis, including lighter hydrocarbons and water, further dilute the reactant gases. The injection of makeup synthesis gas that contains carbon monoxide gas and hydrogen gas can increase the concentration of both reactants in the synthesis gas and therefore increase the rate of reaction.

Appropriate catalysts are those that promote a Fischer-Tropsch synthesis of hydrocarbons. The particular catalyst selected depends on the preferred operating conditions and the desired product, and are typically selected, for example, from iron, cobalt, rare earth catalysts, and mixtures thereof. A preferred catalyst for synthesizing waxy hydrocarbons is a cobalt ruthenium catalyst. The active catalytic metal salts are impregnated or mulled with substrate particles such as alumina. Said catalyst particles and manufacture are known to the art. Said particles must be large enough and dense enough to have a tendency to settle in the substantially inert liquid. In the reaction zone this tendency will be counteracted by the movement of gas and of fluid. In the separation zone, it is very desirable to have the catalyst settle through the liquid and back into the reaction zone.

For an ebullated bed, it is important that the catalyst charge contain neither too large a fraction of large particles nor too large a fraction of small particles. A proper size distribution is important for successful fluidization of the catalyst bed without carryover of catalyst in the withdrawn liquid medium and product. An embodiment contains particulate solid catalyst that has an average particle diameter of between about 0.2 and about 3.5 millimeters. A more preferred embodiment contains particulate solid catalyst that has an average particle diameter of between about 0.3 and about 1.6 millimeters. A preferred size distribution will be narrow.

Typically with a cobalt-based catalyst, contact between the synthesis gas and the catalyst results in the production of largely paraffinic hydrocarbons, along with small amounts of olefins and oxygenates. The product, using such a cobalt-based catalyst, may contain about one half by weight middle range boiling hydrocarbons, about one third by weight of waxy paraffin, and the remainder lighter boiling hydrocarbons and methane. The composition changes somewhat if iron-based catalysts are used. In either case, part of the product will be vaporized into the gas and be carried out of the reactor along with inert compounds and unconverted feed gas. The fraction of the product that is carried out in the vapor phase will depend upon the operating conditions being used. These hydrocarbons may be recovered using methods known to the art. The remaining product will be miscible with the liquid medium.

The substantially inert liquid medium comprises hydrocarbons with a boiling point range above 340° C., i.e. paraffin wax; hydrocarbons with a boiling point range of about 200° C. to about 340° C., herein called midrange boiling hydrocarbons; a product of the synthesis reaction, or mixtures thereof. The fraction of each can be varied to achieve efficient operation. For instance, midrange boiling hydrocarbons minimize foaming. Midrange boiling hydrocarbons lower the solidifying temperature of the mixture, and can allow the liquid to be cooled to a lower temperature than waxy hydrocarbons. A preferred embodiment of the invention contains a substantially inert liquid comprised of from about 0.001% to about 50% midrange boiling hydrocarbons. Waxy paraffinic hydrocarbons can increase the viscosity of the liquid and they are easy to separate from lighter hydrocarbons. The properties of these fractions and the fluid properties that result from mixing them are known to the art. The liquid medium may well have a composition similar to that of the product. A portion of the product of the reaction will mix and may become indistinguishable from the substantially inert liquid medium. Therefore, product hydrocarbons will comprise a fraction of the liquid medium, and after a long period product hydrocarbons may comprise most of the liquid medium. For startup purposes, if there is no product available, $C_{30}$ to $C_{50}$ poly-alpha-olefins or highly refined, i.e. heteroatom and aromatic free, hydrocarbons may be used as the substantially inert liquid medium.

An embodiment of this invention requires partial separation of these components of the withdrawn liquid medium, using separation methods known to the art, and reconstituting and recycling back to the reactor a fraction that has the desired properties. Alternatively, an unfractionated fluid may be recycled to the ebullated bed. A preferred embodiment will allow regulation of the temperature of the substantially inert liquid entering the reactor by employing a heat exchanger external to the reactor to cool the recirculating stream. Typically, the liquid medium withdrawn from the reactor is obtained from the separation zone that is located above the reaction zone. Those skilled in the art will realize that it may also be advantageous to add, and withdraw, fluid directly to, and from, the reaction zone. This will allow greater temperature control and can provide a mechanism for removing or adding catalyst to the bed.

The process pressure can be any pressure sufficient to allow the described reaction. Typically, such pressure is from about 1 atmosphere to about 100 atmospheres, preferably from 10 to 60 atmospheres, and more preferably from 20 to 50 atmospheres. Anything lower than 1 atmosphere would require operation at vacuum conditions which is not necessary and unduly expensive. Pressures greater than about 100 atmospheres would increase the cost significantly due to the increased strength of the equipment necessary to withstand high pressures.

The ebullated bed is operated at a sufficient temperature for Fisher-Tropsch synthesis to occur. While such temperatures depend on many factors, principally the catalyst selected, a typical temperature in the reactor should be from about 150° to about 325° C., and more preferably from about 160° to about 300° C., and most preferably from about 160° to about 240° C. The rate of reaction at temperatures below 150° C. would require an extraordinary amount of catalyst. Temperatures above about 325° C. favors the generation of methane.

The ebullated bed reactor diameter is selected to give a feed gas superficial velocity (actual volumetric flow rate of feed gases at reactor conditions divided by empty cross-sectional area) between about 2 centimeters per second to about 30 centimeters per second. The preferred range is from about 6 centimeters per second to about 20 centimeters per second. The more preferred range is from about 10 centimeters per second to about 20 centimeters per second. The velocity of the gas affects the gas holdup and gas-liquid mass transfer and back-mixing. The preferred gas hourly space velocity selected for optimal reactor conversion efficiency should be between 200 and 20,000 $m^3$ per hour per $m^3$ catalyst, more preferred between 500 and 10,000 $m^3$ per hour per $m^3$ catalyst.

For an ebullated bed reactor the catalyst bed is in part supported by the liquid medium flux. The velocity of recycling liquid should be between about 0.1 and about 20 centimeters per second, more preferred between about 1 and about 10 centimeters per second. The liquid hourly space velocity should be between about 10 and about 100 volumes of liquid per volume of catalyst per hour. The preferred liquid hourly space velocity should be between about 20 to about 80 volumes liquid per volume catalyst per hour.

Because of the exothermic nature of the F-T reaction, the reactor is advantageously equipped with heat removal capabilities so that the desired reaction temperature can be carefully controlled. In an ebullated bed reactor, heat can be removed in a variety of ways, including decreases in the sensible heat of the feed, internal heat exchangers, and external heat exchangers. Inclusion of each of these methods is a preferred embodiment of the invention.

A preferred means of regulating the temperature of the reactor comprises employing an internal heat exchanger which comprises a tube. Those skilled in the art will know that heat exchangers often employ multiple tubes, in series and in parallel, and these are included in this description. Said tube may also have vanes or other devices known in the art to facilitate heat transfer between the ebullated bed and the cooling fluid. The cooling medium enters the tube from outside the reactor vessel. In a more preferred embodiment the cooling medium entering the tube comprises a liquid which is at least partially vaporized within the tube. Such cooling liquids include, for example, hydrocarbon based liquids, the commercially available Dowtherm, halogenated hydrocarbons, and water. The most preferred embodiment uses Dowtherm, water, glycols, and mixtures thereof, which are introduced to the tube in liquid form and are at least partially vaporized prior to withdrawing these liquids from the tube.

Other heat exchangers known to the art, including external heat exchanger jackets, may be included.

Another preferred means for removing heat from the reactor is to introduce liquid medium to the reactor at a temperature below the reactor temperature. To the extent that the liquid medium introduced is recycled liquid medium, a heat exchanger must be utilized to cool the liquid. Heat exchangers that remove heat from liquids are well known to the art.

In addition to the above described means of removing heat, the substantially inert liquid medium acts as a heat sink. With conventional gas-phase processes, the heat released during reaction substantially increases the gas and catalyst temperature, which impedes the hydrocarbon synthesis reaction, increases methanation, and causes catalyst deactivation or destruction. The high thermal capacity of the liquid phase permits high conversions while moderating temperature gains. The heat is transferred to the fluid and the fluid facilitates removal of the heat.

The synthesis gases may be preheated before entering the reactor. Because the F-T reaction is highly exothermic, it is not normally necessary to heat the feed gas all the way to reaction temperature. The gas can also be heated by the substantially inert liquid in the reactor.

The above described invention has many advantages. It provides several effective means of controlling temperature, thereby allowing higher conversions in the reactor without excessive methanation or destruction of the catalyst. It provides a means for controlling the hydrogen gas to carbon monoxide gas ratio, thereby providing a mechanism for maximizing reaction rates and reaction selectivity throughout the reaction zone. It allows for high reaction bed height because the catalyst is buoyed by gas and also possibly by liquid, which will reduce catalyst crushing for a given catalyst load. This invention also utilizes the maximum reactor volume, since plates that can be employed to support catalyst and to redistribute fluids are not present in this invention. Another advantage is that an ebullated bed has nearly zero pressure differential across the reaction zone thereby providing a more uniform pressure that improves productivity and selectivity to $C_5$+hydrocarbons.

Figure 1:
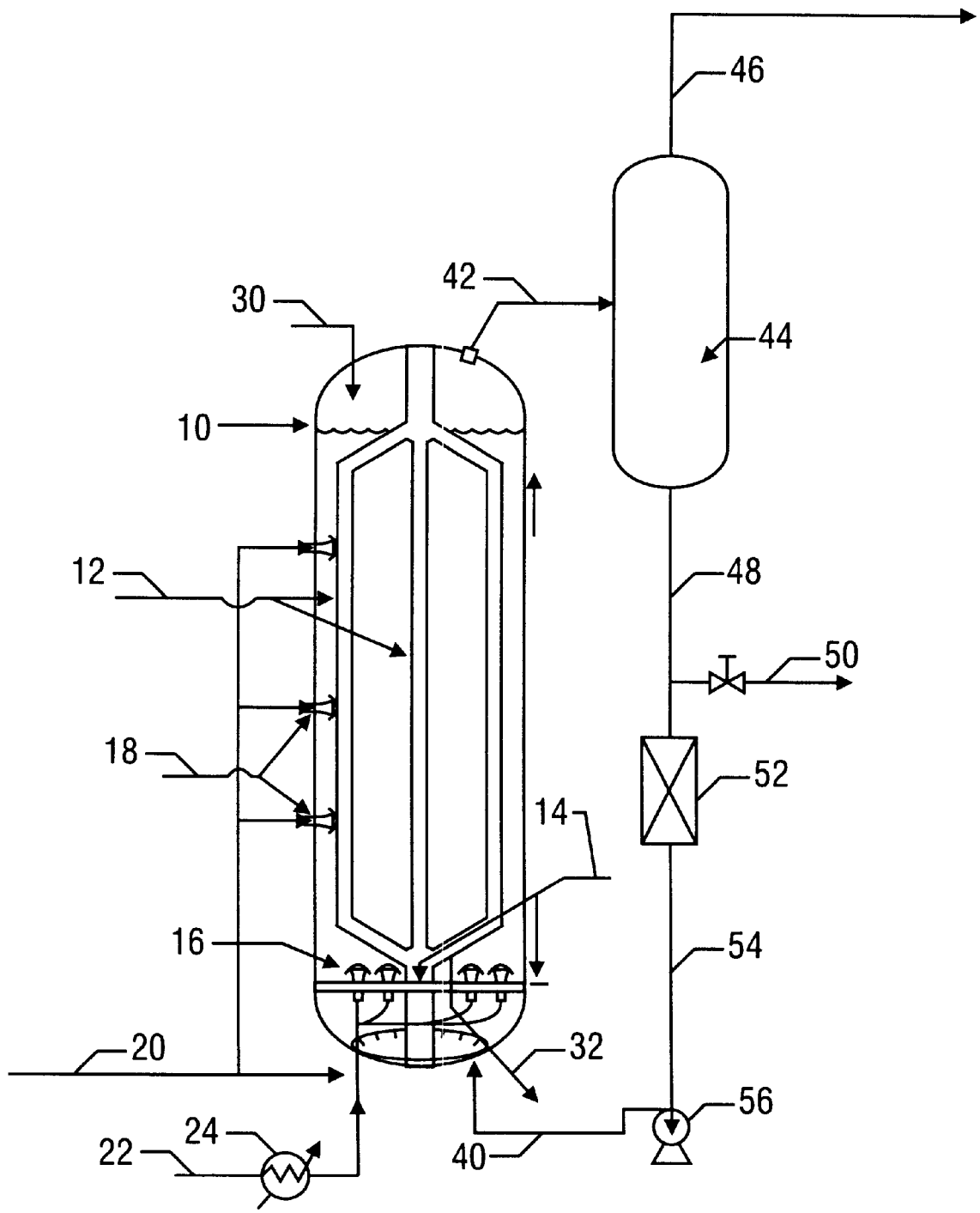
FIG. 1 is a schematic diagram of an ebullated bed reactor for conversion of synthesis gas to liquid hydrocarbons A commercial embodiment of the F-T synthesis process can be optimized to produce principally fuels and lubricants as products.

FIG. 1 is a schematic diagram of an ebullated bed reactor for conversion of synthesis gas to liquid hydrocarbons. The reaction zone extends from this diffuser to about the point where the internal reactor heat exchangers exit the catalyst bed. Above the reaction zone is a separation zone. An approximate location for the transition from the reaction zone to the separation zone is shown by the wavy line opposite arrow 10.

The synthesis gas enters the ebullated bed 10 via line 22. The synthesis gas may be preheated in heat exchanger 24. The synthesis gas is introduced into the reaction zone via spargers 16 located in or around the base plate 14 or bottom of the reaction zone or, alternatively, via a transverse distributor plate also depicted as item 14. Three single spargers are in place to add, in this embodiment, a gas comprising hydrogen gas into the reaction zone. The synthesis gas may be supplemented with hydrogen enriched gas from line 20. Line 20 also supplies hydrogen enriched gas to the reaction zone via spargers 18 located in the reaction zone. An internal cooling coil or coils 12 may pass through the reaction zone, but do not interfere with the introduction of gas via spargers 16 and 18 or with the vertical migration of fluid.

Substantially inert fluid is introduced to the ebullated bed reactor 10 via an ebullating pump 56 and line 40. The fluid may flow up through openings in the base plate 14 or alternatively may be introduced with the gas via the transverse distributor plate 14. The liquid medium and gas leave the reactor and are separated from one another in the hot separator. Fluids and gas exit the ebullating bed reactor 10 via line 42. If the separation zone is large then the fluids may exit the ebullated bed as separate gas and fluid streams. In this embodiment, however, the fluids and gas then pass to a hot separator 44 which may be operated at reduced pressure. By controlling hot separator pressure and temperature, the composition of the recycled liquids can be varied.

The substantially inert fluid exits the hot separator via line 48, and a portion may be withdrawn as product via line 50. The remaining fluid may be cooled with a heat exchanger 52 and then pass via line 54 back to the ebullating pump 56.

Catalyst may be added to the reaction zone via, for example line 30 and withdrawn from the reaction zone via line 32.

Figure 2:
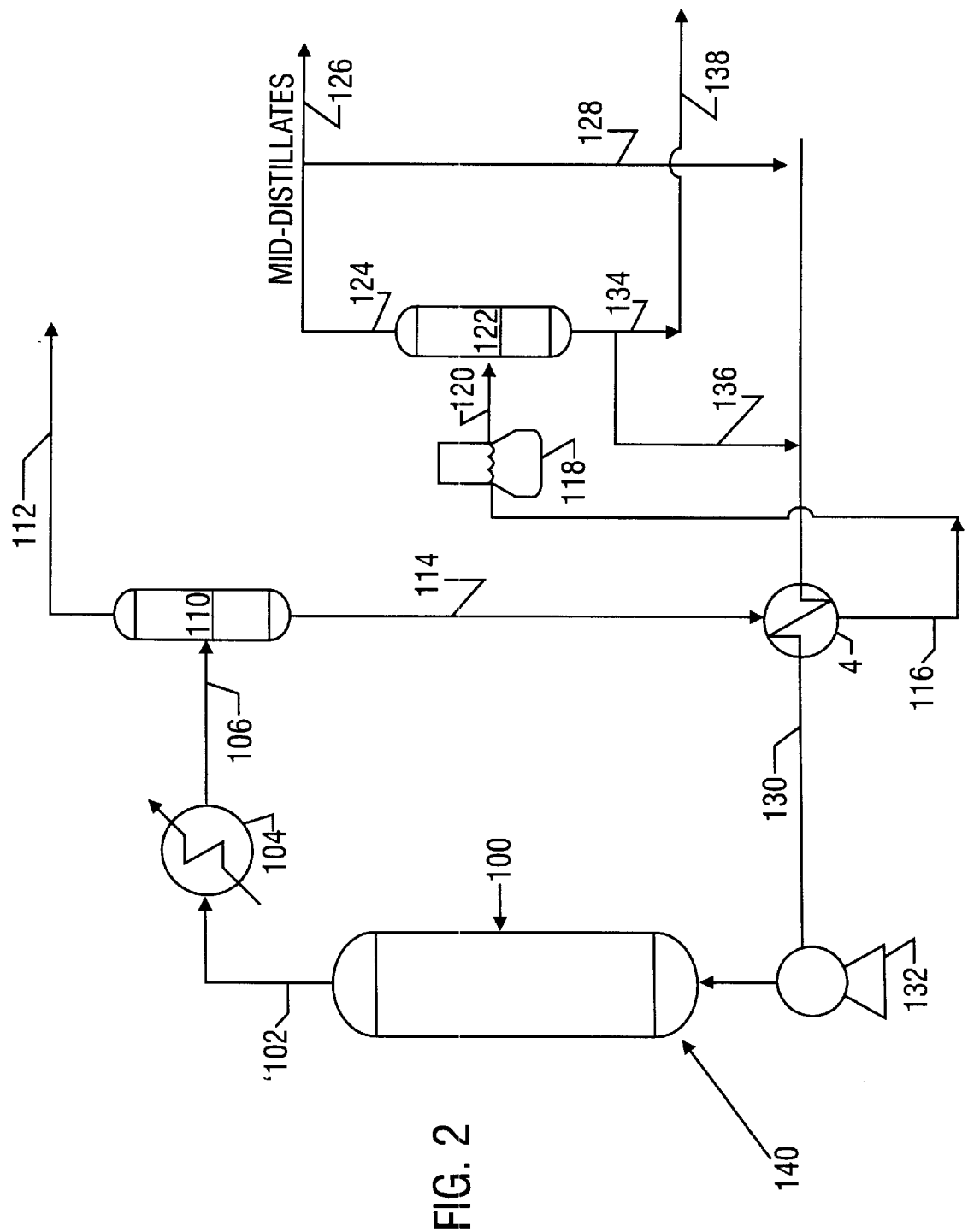
FIG. 2 is a schematic of such a process wherein the ebullated bed reactor 1 is designed for very high conversion at a single throughput. The reactor internals are similar to those shown in FIG. 1 and are not shown herein.

A commercial embodiment of the F-T synthesis process can be optimized to produce principally fuels and lubricants as products. FIG. 2 is a schematic of such a process wherein the ebullated bed reactor 100 is designed for very high conversion at a single throughput. The reactor internals are similar to those shown in FIG. 1 and are not shown herein.

This embodiment of the invention shows synthesis gas entering the ebullated bed reactor 100 via line 140. The details of the ebullated bed are omitted in this figure. The fluids exit the ebullated bed reactor via line 102 and are optionally cooled in heat exchanger 104. The fluids then pass to the separation vessel 110 via line 106. Gases and light naphtha are withdrawn from the top of the separation vessel 110 via line 112. Heavier hydrocarbons exit the separation vessel via line 114 and are optionally cooled in heat exchanger 4. The fluids leave the heat exchanger via line 116 to knockout vessel 118 and then via line 120 to the second separation vessel 122. Mid-distillates are withdrawn via line 124, a portion is separated as product via line 126, and a portion is optionally recycled to the ebullated bed via line 128, through heat exchanger 4, and through the ebullating pump 132. The recycled liquids via line 130, is a mixture, which can be varied, by controlling the relative flows of liquid through lines 128 and 136. Recycled liquids via line 130, are preferably of a boiling point sufficiently higher than reaction temperature so as to not produce significant vapor phase.

Another preferred commercial application of the F-T synthesis process produces principally fuels as products. FIG. 3 is a schematic of such a process wherein three reactors in series are used to process the feed synthesis gas. The F-T synthesis occurs in the first two reactors.

This embodiment of the invention incorporates several ebullated bed reactors. Synthesis gas enters the ebullated bed reactor 202 via line 200. The details of the ebullated bed are omitted in this figure. The fluids exit the ebullated bed reactor via line 204 and then pass to the separation vessel 206. Gases and light naphtha are withdrawn from the top of the separation vessel 206 via line 208. Not shown in FIG. 3 is the separation and removal of contaminants, principally water vapor, from the vapors that exit the hot separator 4 via line 103. Water vapor content above 50% in the gas phase seriously impedes the F-T synthesis process. Heavier hydrocarbons exit the separation vessel 206 via line 210 and a portion are conveyed to the heat exchanger 212. The fluids leave the heat exchanger to the ebullating pump 214 and are recycled to the ebullated bed 202. The unconverted feed gases are mixed with a fraction of liquid components and introduced to the second ebullated bed reactor. A fraction of the heavier hydrocarbons from line 210 are optionally commingled with gases and naphtha from line 208 and are fed via line 218 to the second ebullated bed reactor 220. Additional synthesis gas and hydrogen enriched gas feed lines to the reactor 220 are not shown. The fluids exit the ebullated bed reactor 220 via line 222 and then pass through a heat exchanger 224. The cooled fluids pass via line 226 to the separation vessel 228. Gases and light naphtha are withdrawn from the top of the separation vessel 228 via line 230 and are separated as product, used as fuel, or used for other processes. Heavier hydrocarbons exit the separation vessel 228 via line 232 and are further cooled in heat exchanger 234. The fluids then pass via line 236 to a settling vessel 238 and then to a separation vessel 240. Mid-distillates are withdrawn from the top via line 242. A portion is separated as product in line 244, and a portion passes via line 246 through heat exchanger 234 to be heated. This fluid when mixed with liquids from line 258 then passes through the ebullating pump 248 and are recycled via line 250 to the ebullated bed 220. The higher boiling fraction from the hot separator is mixed with hydrogen and stream and is introduced to the third ebullated reactor. The function of this third reactor is not an F-T synthesis but rather to convert high molecular weight hydrocarbons into lower molecular weight hydrocarbons. The heavy hydrocarbons exiting separation vessel 240 via line 252 are supplemented with hydrogen and steam feed from line 254 and are conveyed via line 256 to a cracking unit 260. Hydrocarbons leaving the cracking unit 260 via line 262 are fractionated in vessel 264 and gases and naphtha are withdrawn via line 266. Heavier hydrocarbons leave separation vessel 264 via line 268 and a portion is withdrawn as mid-distillates product and a portion is recycled through ebullating pump 274 to the cracking unit 260.

EXAMPLES

As an example, 1000 standard cubic feet per hour of synthesis gas containing 46.8 mole percent nitrogen, 33.1 mole percent hydrogen, 16.8 mole percent carbon monoxide, 2.9 mole percent carbon dioxide, and 0.32 mole percent water vapor is contacted with 0.61 cubic feet of a cobalt ruthenium catalyst on alumina support at an average reactor temperature of 204° C., a pressure of 370 psi, and a gas hourly space velocity of 1650 cubic feet per hour per cubic feet of catalyst. An 85% conversion of the carbon monoxide to hydrocarbons is achieved at these conditions in a single pass through the reactor. The resulting hydrocarbon product distribution is shown below:

|  | lb/hr | wt % |
| --- | --- | --- |
| Methane | 0.45 | 8.08 |
| Ethane | 0.11 | 1.90 |
| Propane | 0.14 | 2.57 |
| Normal Butane | 0.17 | 3.04 |
| Normal Pentane | 0.19 | 3.42 |
| C6–C12 | 1.51 | 27.28 |
| C13–C19 | 1.28 | 23.10 |
| C20+ | 1.70 | 30.61 |

What is claimed is:

1. In a process for producing hydrocarbons from hydrogen and carbon monoxide by reacting hydrogen and carbon monoxide in a reaction zone comprising particulate solid catalyst and substantially inert liquid medium, the improvement comprising:

conducting the reaction in a single turbulent reaction zone within an ebullated bed reactor vessel adapted for the reaction of gases in the presence of a substantially inert liquid medium and solid particulate catalyst wherein gas comprising one or more of hydrogen gas and carbon monoxide gas are introduced at a plurality of locations within the reaction zone such that bubbles of the gases flow upward through the reaction zone comprising solid catalyst particles and substantially inert liquid medium at sufficient velocity to expand the bed to a volume greater than its static volume.

2. The process of claim 1 wherein the substantially inert liquid medium is both added and withdrawn from the reaction zone, thereby creating a flux which facilitates the expansion of the bed to the point wherein at least some of the solid catalyst is in a state of random motion.

3. The process of claim 2 wherein each location where hydrogen gas or carbon monoxide gas, or both, is introduced is located within the reactor vessel at a predetermined distance from the bottom of the vessel.

4. The process of claim 3 wherein at least one of the locations, where the location is determined by the distance from the bottom of the reactor, where the hydrogen gas or carbon monoxide gas, or both gases, is introduced dispenses the gas at a plurality of points located at approximately the same distance from the bottom of the reactor vessel, and at approximately equidistant from a vertical axis defined by the center of a horizontal cross section of the reactor vessel.

5. The process of claim 1 wherein the gas is introduced through an apparatus which comprises a tubular portion extending inward through the wall of the reactor and a sparger portion, said sparger portion being attached to the tubular portion, and dispensing gas at a location within the turbulent reaction zone.

6. The process of claim 2 wherein the diameter of the bubbles of synthesis gas is less than about 5 millimeters.

7. The process of claim 2 wherein the liquid medium is selected from the group consisting of paraffin wax, hydrocarbons with a boiling point of from about 150° C. to about 340° C., and mixtures thereof.

8. The process of claim 2 wherein there are means for modifying the liquid medium or catalyst, or both, while the reaction is proceeding.

9. The process of claim 2 wherein at least a portion of the liquid medium that is withdrawn is recycled.

10. The process of claim 9 wherein the concentration of middle distillate fraction having a boiling point range of 200° C. to about 340° C. in the recycled liquid medium is from about 0.001 to about 50 volume percent.

11. The process of claim 1 wherein the solid particulate catalyst has an average particle diameter of from about 0.2 to about 3.5 millimeters.

12. The process of claim 1 wherein the solid particulate catalyst has an average particle diameter of from about 0.3 to about 1.6 millimeters.

13. The process of claim 3 wherein the molar ratio of hydrogen to carbon monoxide is in the reaction zone from about 0.5:1 to about 6.0:1.

14. The process of claim 13 wherein the molar ratio of hydrogen to carbon monoxide is in the reaction zone from about 1.0:1 to about 3.0:1.

15. The process of claim 14 wherein the molar ratio of hydrogen to carbon monoxide is in the reaction zone from about 1.6:1 to about 2.2:1.

16. The process of claim 2, wherein the reactor vessel comprises a means for removing heat.

17. The process of claim 16 wherein the means for removing heat comprises a tube arranged such that a cooling medium may enter and exit the tube from outside the reactor vessel.

18. The process of claim 17 wherein the cooling medium entering the tube comprises a liquid which is at least partially vaporized within the tube.

19. The process of claim 18 wherein the cooling medium is selected from group consisting of Dowtherm, water, glycols, and mixtures thereof.

20. The process of claim 9, further comprising means external to the reactor vessel for removing heat from the liquid medium that is recycled.

21. The process of claim 2, wherein the gas space velocity is between about 200 and about 20,000 cubic meters per cubic meter of catalyst per hour.

22. The process of claim 21 wherein the gas space velocity is between about 500 and about 10,000 cubic meters per cubic meter of catalyst per hour.

23. The process of claim 2 wherein the liquid flux is between about 1 and about 10 centimeters per second.

24. The process of claim 2 wherein the liquid space velocity is between about 10 and about 100 cubic meters of substantially inert liquid per cubic meter of catalyst per hour.

25. The process of claim 2 wherein the liquid space velocity is between about 20 and about 80 cubic meters of substantially inert liquid per cubic meter of catalyst per hour.

26. The process of claim 3 wherein hydrogen gas, carbon monoxide gas, or a mixture thereof is introduced at from 3 to 8 predetermined distances from the bottom of the vessel.

27. The process of claim 3 wherein hydrogen gas, carbon monoxide gas, or a mixture thereof is introduced at from 6 to 7 predetermined distances from the bottom of the vessel.

* * * * *